United States Patent [19]

May

[11] 3,970,656
[45] July 20, 1976

[54] 1-ALKYL-4-M-HYDROXYPHENYL-4-PROPIONYL PIPERIDINES

[75] Inventor: Everette Lee May, Bethesda, Md.

[73] Assignee: Government of the United States, Washington, D.C.

[22] Filed: June 11, 1974

[21] Appl. No.: 478,547

[52] U.S. Cl............................. 260/293.8; 424/267; 260/293.75
[51] Int. Cl.² ....................................... C07D 211/32
[58] Field of Search ................................. 260/293.8

[56] References Cited
OTHER PUBLICATIONS
Grumbach et al., J. Pharm. & Exptl. Therap., 149:385–396, (1965).
Kutter, J. Med. Chem., 13: 801–805, (1970).

*Primary Examiner*—Sherman D. Winters
*Attorney, Agent, or Firm*—Samuel L. Welt; Bernard S. Leon; William G. Isgro

[57] ABSTRACT

Phenylpiperidines of the formula

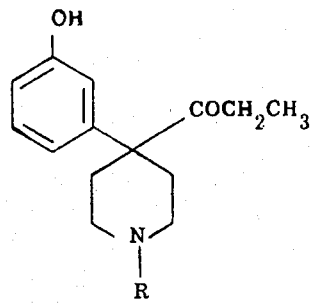

wherein R is alkyl of 4 to 7 carbon atoms are described. The foregoing phenylpiperidines are useful as non-addicting analgesics.

5 Claims, No Drawings

1-ALKYL-4-M-HYDROXYPHENYL-4-PROPIONYL PIPERIDINES

BRIEF SUMMARY OF THE INVENTION

The invention relates to phenylpiperidines of the formula

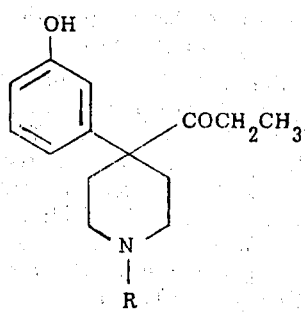

I wherein R is alkyl of 4 to 7 carbon atoms or pharmaceutically acceptable acid addition salts thereof. The compounds of formula I are useful as non-addicting analgesics.

DETAILED DESCRIPTION OF THE INVENTION

As used herein, the term "alkyl of 4 to 7 carbon atoms" is understood to mean straight or branched chain alkyl of 4 to 7 carbon atoms, such as, butyl, isobutyl, amyl, isoamyl, hexyl, heptyl or the like.

The compounds of the invention are characterized by the formula

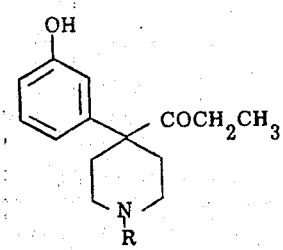

wherein R is straight or branched chain alkyl of 4 to 7 carbon atoms. The compounds of formula I form acid addition salts and such salts are also within the scope of this invention. Thus, the compounds of formula I form pharmaceutically acceptable acid addition salts with, for example, both pharmaceutically acceptable organic and inorganic acids, such as, acetic acid, succinic acid, formic acid, methanesulfonic acid, p-toluenesulfonic acid, nitric acid, phosphoric acid, sulfuric acid, hydrochloric acid, hydrobromic acid and the like.

Exemplary of the compounds of formula I are:
1-butyl-4-m-hydroxyphenyl-4-propionylpiperidine;
1-amyl-4-m-hydroxyphenyl-4-propionylpiperidine;
1-hexyl-4-m-hydroxyphenyl-4-propionylpiperidine;
1-heptyl-4-m-hydroxyphenyl-4-propionylpiperidine;
and the like.

A preferred compound of the invention is 1-amyl-4-m-hydroxyphenyl-4-propionylpiperidine.

The compounds of formula I are prepared by treating 4-m-methoxyphenyl-4-propionylpiperidine or its salts, for example, the hydrochloride, with an alkyl iodide or bromide, wherein the alkyl group is a straight or branched chain alkyl of 4 to 7 carbon atoms, in an inert organic solvent, such as 2-butanone, dimethylformamide or the like. The reaction is carried out at a temperature in the range of from about 80° to about 120°; preferably, the reflux temperature of the reaction mixture.

The resultant N-alkyl methyl ether is then treated with 48% HBr at reflux to obtain the corresponding phenylpiperidine of formula I.

The 4-m-methoxyphenyl-4-propionylpiperidine starting material can be prepared from 4-m-methoxyphenyl-1-methyl-4-propionylpiperidine as hereinafter described in Example 2.

The 4-m-methoxyphenyl-1-methyl-4-propionylpiperidine precursor can be prepared according to known procedures, see for instance, Example 1 and A. W. D. Avison and A. L. Morrison, J. Chem. Soc., 1470 (1950).

The compounds of formula I, as well as their pharmaceutically acceptable acid addition salts, are useful as non-addicting analgesic agents.

The useful analgesic activity of the compounds of formula I can be demonstrated in warm blooded animals utilizing standard procedures. Exemplary of such procedures are (1) Hot-plate test — T. D. Perrine, L. Atwell, I. B. Tice, A. E. Jacobson and E. L. May, J. Pharm. Sci., 61, 86 (1972), (2) Nilsen test — T. D. Perrine et al., supra, and (3) Physical Dependence Capacity Test in rhesus monkeys — J. E. Villareal, "Advances in Mental Science", Vol. II, R. T. Harris, W. McIsaac and C. R. Schuster, Ed., University of Texas Press, Houston, Texas, 1970, pp. 83–116. When compounds of the invention are utilized as the test substances in the foregoing tests the results set forth in Table I are obtained.

TABLE I

| Compound[a] | Hot-plate | Nilsen | PDC[b] | Antagonist Activity |
| --- | --- | --- | --- | --- |
| 1-butyl-4-m-hydroxyphenyl 4-propionylpiperidine | 1.7 | | Low | No |
| 1-amyl-4-m-hydroxyphenyl- 4-propionylpiperidine | 0.3 | 0.4 | No | Yes |
| 1-hexyl-4-m-hydroxyphenyl- 4-propionylpiperidine | 3.0 | 2.4 | No | Yes |
| 1-heptyl-4-m-hydroxyphenyl- 4-propionylpiperidine | 3.7 | 3.5 | No | Yes |

[a] administered as the hydrobromide salt
[b] physical dependence capacity

The products of the invention can be incorporated into standard pharmaceutical dosage forms, for example, they are useful for oral or parenteral application with the usual pharmaceutical adjuvant material, e.g., organic or inorganic inert carrier materials such as water, gelatin, lactose, starch, magnesium stearate, talc, vegetable oils, gums, polyalkylene-glycols, Vaseline, etc. The pharmaceutical preparations can be employed in a solid form, e.g., as tablets, troches, suppositories, capsules, or in liquid form, e.g., as solutions, suspensions or emulsions. The pharmaceutical adjuvant material can include preservatives, stabilizers, wetting or emulsifying agents, salts to change the osmotic pressure or to act as buffers. They can also contain other therapeutically active materials.

The following examples further illustrate the invention. All temperatures are in degrees Centigrade, unless otherwise mentioned.

EXAMPLE 1

Preparation of 1-m-methoxyphenyl-1-propionoxypiperidine

To the Grignard reagent prepared (in diethylether) from 23.4 g. of Magnesium and 150 g. of ethyl iodide was added (efficient stirring) 55 g. of 4-cyano-4-m-methoxyphenyl-1-methylpiperidine in 400 ml. of benzene. The diethylether was distilled and the mixture was refluxed for 1 hour. After cooling, 80 g. of ammonium chloride in water was added. The separated organic layer was washed with dilute potassium hydroxide and refluxed for 30 minutes with 600 ml. of 2N HCl. The aqueous layer was separated, washed with benzene, made alkaline with potassium hydroxide pellets, and extracted with benzene. The extract was dried with $Na_2SO_4$ and evaporated to give an oil (46 g.); b.p. 160°–161° (2mm); yield 40.5 g. (65%); $\nu$1710 $cm^{-1}$.

EXAMPLE 2

Preparation of 4-m-methoxyphenyl-1-propionylpiperidine hydrochloride

To a stirred solution of 25 g. of ethyl chloroformate in 80 ml. of benzene was added 20.5 g. of 1-m-methoxyphenyl-1-methyl-1-propionoxypiperidine in 100 ml. of benzene during 30 minutes. The mixture was refluxed for 2 hours, washed with water and then 10% HCl, dried with $Na_2SO_4$ and evaporated to dryness to give 23 g. (90%) of oily carbamate; $\nu$1710–1705, $1250^{cm-1}$. From the water and acid washings 2 g. (10%) of 1-m-methoxyphenyl-1-methyl-1-propionoxypiperidine was recovered.

The 23 g. of carbamate and 300 ml. of 23% HCl were refluxed together for 12.5 hr., washed with benzene, made alkaline with sodium hydroxide pellets, and extracted with benzene. Drying and evaporation of the benzene gave 11.6 g. of an oil which was converted to the hydrochloride. Recrystallization from ethyl alcohol gave 11.5 g. (52%) of plates: mp 205°–207°; $\nu$ Nujol 1700 $cm^{-1}$. Anal. $(C_{15}H_{22}ClNO_2)$C,H,Cl,N.

EXAMPLE 3

Preparation of 1-butyl-4-m-hydroxyphenyl-4-propionylpiperidine hydrobromide 1.6 g. of butyl iodide, 2.0 g. of 4-m-methoxyphenyl-4-propionylpiperidine hydrochloride, 3.0 g. of potassium bicarbonate and 50 ml. of 2-butanone were refluxed (stirring) for 5 hours and evaporated to dryness. The residue was treated with chloroform and water. The chloroform layer was washed with water, dried over sodium sulfate and evaporated to given an oil. The oil and 6 ml. of 48% hydrogen bromide were refluxed for 30 minutes and evaporated to dryness in vacuo. Recrystallization of the residue from ethanol gave in 89% yield 1-butyl-4-m-hydroxyphenyl-4-propionylpiperidine hydrobromide melting point 217°–218°.

EXAMPLE 4

Preparation of 1-amyl-4-m-hydroxyphenyl-4-propionylpiperidine hydrobromide 0.6 g. of amylbromide, 1 g. of 4-m-methoxyphenyl-4-propionylpiperidine hydrochloride, 1.5 g. of potassium bicarbonate and 25 ml. of dimethylformamide were kept at 90° for 6 hours and evaporated to dryness in vacuo; the residue was treated with chloroform and water. Evaporation of the chloroform layer gave 1.1 g. of oil which was demethylated with 5 ml. of 48% hydrobromic acid (30 minute reflux). Distillation to dryness in vacuo and recrystallization of the residue from isopropyl alcohol gave 1.1 g. (83%) of 1-amyl-4-m-hydroxyphenyl-4-propionylpiperidine hydrobromide having a melting point of 189.5°–190°.

EXAMPLE 5

Preparation of 1-hexyl-4-m-hydroxyphenyl-4-propionylpiperidine hydrobromide

As described in the preparation of 1-amyl-4-m-hydroxyphenyl-4-propionyl-hydrobromide (Example 4), the hydrobromide of 1-hexyl-4-m-hydroxyphenyl-4-propionylpiperidine was obtained in 85% yield from hexyl bromide and 4-m-methoxyphenyl-4-propionylpiperidine hydrochloride (15 hours, 80°), and had a melting point of 179°–181°.

EXAMPLE 6

Preparation of 1-heptyl-4-m-hydroxyphenyl-4-propionylpiperidine hydrobromide 1-Heptyl-4-m-hydroxyphenyl-4-propionylpiperidine hydrobromide was obtained in 78% yield, as described for the procedure for obtaining 1-hexyl-4-m-hydroxyphenyl-1-propionylpiperidine hydrobromide, using heptyl bromide; plates, melting point 147°–149°, from acetone.

EXAMPLE 7

Preparation of Tablets

Tablet Formulation

| | Per Tablet |
|---|---|
| 1-Amyl-4-m-hydroxyphenyl-4-propionyl-piperidine hydrobromide | 100 mg. |
| Lactose, U.S.P. | 202 mg. |
| Corn Starch, U.S.P. | 80 mg. |
| Amijel BO11* | 20 mg. |
| Calcium Stearate | 8 mg. |
| Total Weight | 410 mg. |

*A prehydrolyzed food grade corn starch. Any similar prehydrolyzed corn starch may be used.

PROCEDURE

1-Amyl-4-m-hydroxyphenyl-4-propionyl-piperidine hydrobromide, lactose, corn starch and Amijel BO11 are blended in a suitable mixer. The mixture is granulated to a heavy paste with water and the moist mass is passed through a No. 12 screen. It is then dried overnight at 100°F. The dried granules are passed through a No. 16 screen and transferred to a suitable mixer. The calcium stearate is added and mixed until uniform. The mixture is compressed at a tablet weight of 410 mg. using tablet punches having a diameter of approximately ⅜ inch. (Tablets may be either flat or biconvex and may be scored if desired.)

EXAMPLE 8

Preparation of Tablets

Tablet Formulation

| | Per Tablet |
|---|---|
| 1-Amyl-4-m-hydroxyphenyl-4-propionyl-piperidine hydrobromide | 25 mg. |
| Dicalcium Phosphate Dihydrate, Unmilled | 175 mg. |
| Corn Starch | 24 mg. |
| Magnesium Stearate | 1 mg. |
| Total Weight | 225 mg. |

PROCEDURE

1-Amyl-4-m-hydroxyphenyl-4-propionyl-piperidine hydrobromide and corn starch are mixed together and passed though a No. 00 screen in Model "J" Fitzmill with hammers forward. This premix is then mixed with dicalcium phosphate and one-half of the magnesium stearate, passed through a No. 1A screen in Model "J". The slugs are passed through a No. 2A plate in a Model "D" Fitzmill at slow speed with knives forward, and the remaining magnesium stearate is added. The mixture is mixed and compressed.

EXAMPLE 9

Preparation of Capsules

Capsule Formulation

| | Per Capsule |
|---|---|
| 1-Amyl-4-m-hydroxyphenyl-4-propionyl-piperidine hydrobromide | 50 mg. |
| Lactose, U.S.P. | 125 mg. |
| Corn Starch, U.S.P. | 30 mg. |
| Talc, U.S.P. | 5 mg. |
| Total Weight | 210 mg. |

PROCEDURE

1-Amyl-4-m-hydroxyphenyl-4-propionyl-piperidine hydrobromide is mixed with lactose and corn starch in a suitable mixer. The mixture is further blended by passing through a Fitzpatric Comminuting Machine with a No. 1A screen with knives forward. The blended powder is returned to the mixer, the talc added and blended thoroughly. The mixture is filled into No. 4 hard shell gelatin capsules on a Parke Davis capsulating machine.

I claim:

1. A compound of the formula

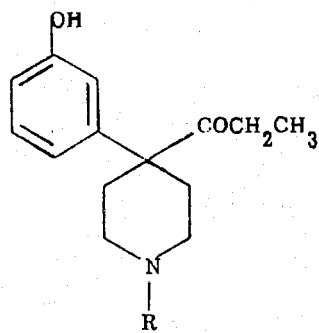

wherein R is alkyl of 4 to 7 carbon atoms or a pharmaceutically acceptable acid addition salt thereof.

2. The compound in accordance with claim 1, 1-butyl-4-m-hydroxyphenyl-4-propionylpiperidine.

3. The compound in accordance with claim 1, 1-amyl-4-m-hydroxyphenyl-4-propionylpiperidine.

4. The compound in accordance with claim 1, 1-hexyl-4-m-hydroxyphenyl-4-propionylpiperidine.

5. The compound in accordance with claim 1, 1-heptyl-4-m-hydroxyphenyl-4-propionylpiperidine.

* * * * *